United States Patent
Yamanaka et al.

(10) Patent No.: US 10,466,234 B2
(45) Date of Patent: Nov. 5, 2019

(54) METHOD OF PRODUCING LABELED ANTIBODY

(71) Applicant: FURUKAWA ELECTRIC CO., LTD., Tokyo (JP)

(72) Inventors: Nobumitsu Yamanaka, Tokyo (JP); Hideki Aizawa, Tokyo (JP); Michio Ohkubo, Tokyo (JP); Kazutomi Miyoshi, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 796 days.

(21) Appl. No.: 14/816,836

(22) Filed: Aug. 3, 2015

(65) Prior Publication Data

US 2015/0338395 A1 Nov. 26, 2015

Related U.S. Application Data

(63) Continuation of application No. PCT/JP2014/051990, filed on Jan. 29, 2014.

(30) Foreign Application Priority Data

Feb. 4, 2013 (JP) ................................. 2013-019972

(51) Int. Cl.
| | | |
|---|---|---|
| *G01N 33/53* | (2006.01) | |
| *G01N 33/543* | (2006.01) | |
| *G01N 33/533* | (2006.01) | |
| *G01N 33/552* | (2006.01) | |
| *G01N 33/532* | (2006.01) | |

(52) U.S. Cl.
CPC ......... *G01N 33/533* (2013.01); *G01N 33/532* (2013.01); *G01N 33/54346* (2013.01); *G01N 33/54353* (2013.01); *G01N 33/552* (2013.01); *Y10T 428/2982* (2015.01)

(58) Field of Classification Search
CPC .............................. G01N 33/53; G01N 44/543
See application file for complete search history.

(56) References Cited

U.S. PATENT DOCUMENTS

| | | | |
|---|---|---|---|
| 4,671,958 A | 6/1987 | Rodwell et al. | |
| 8,993,345 B2 * | 3/2015 | Aizawa | G01N 33/54346 436/172 |
| 2004/0014060 A1 | 1/2004 | Hoheisel et al. | |
| 2009/0017561 A1 | 1/2009 | Aizawa et al. | |
| 2009/0297615 A1 | 12/2009 | Wang et al. | |
| 2010/0310872 A1 * | 12/2010 | Nakamura | A61K 9/1676 428/405 |
| 2011/0136143 A1 | 6/2011 | Castro et al. | |
| 2011/0171320 A1 * | 7/2011 | Dantus | A61K 9/0048 424/617 |
| 2011/0195852 A1 | 8/2011 | Walt et al. | |
| 2012/0045850 A1 * | 2/2012 | Aimiya | B82Y 15/00 436/501 |
| 2014/0051186 A1 | 2/2014 | Aizawa et al. | |
| 2014/0114054 A1 | 4/2014 | Kurosawa et al. | |
| 2016/0153981 A1 * | 6/2016 | Nishida | G01N 33/552 436/501 |

FOREIGN PATENT DOCUMENTS

| | | |
|---|---|---|
| CN | 102105175 A | 6/2011 |
| EP | 1282824 B1 | 3/2006 |
| JP | 2008-304401 A | 12/2008 |
| JP | 2009-516199 A | 4/2009 |
| JP | 2010-100542 A | 5/2010 |
| JP | 2010-538260 A | 12/2010 |
| JP | 2012-198062 A | 10/2012 |
| WO | WO 2006/070582 A1 | 7/2006 |
| WO | WO 2007/061793 A2 | 5/2007 |
| WO | WO 2009/029073 A1 | 3/2009 |
| WO | WO 2012/078868 A1 | 6/2012 |
| WO | WO 2012/147774 A1 | 11/2012 |
| WO | WO 2012/153707 A1 | 11/2012 |

OTHER PUBLICATIONS

Chinese Office Action and Search Report for Chinese Application No. 201480007178.7, dated Apr. 1, 2016, with English Translation.
International Search Report issued in PCT/JP2014/051990, dated May 13, 2014.
Taiwanese Office Action dated Feb. 17, 2016, for Taiwanese Application No. 103103705 with the English Translation.

\* cited by examiner

*Primary Examiner* — Tracy Vivlemore
*Assistant Examiner* — Nam P Nguyen
(74) *Attorney, Agent, or Firm* — Birch, Stewart, Kolasch & Birch, LLP

(57) ABSTRACT

A method of producing a labeled antibody, including the steps of:
 a) allowing silica nanoparticles containing a functional molecule and having a thiol group on a surface thereof, and a linker molecule containing a maleimido group and an amino group, to coexist in a solvent to form a thioether bond between the thiol group and the maleimido group, thereby obtaining functional molecule-containing silica nanoparticles on which the linker molecule is bonded; and
 b) allowing the functional molecule-containing silica nanoparticles on which the linker molecule is bonded, carbodiimide and an antibody to coexist in an aqueous solvent to form an amide bond between the amino group of the linker molecule and a carboxyl group of the antibody.

10 Claims, 1 Drawing Sheet

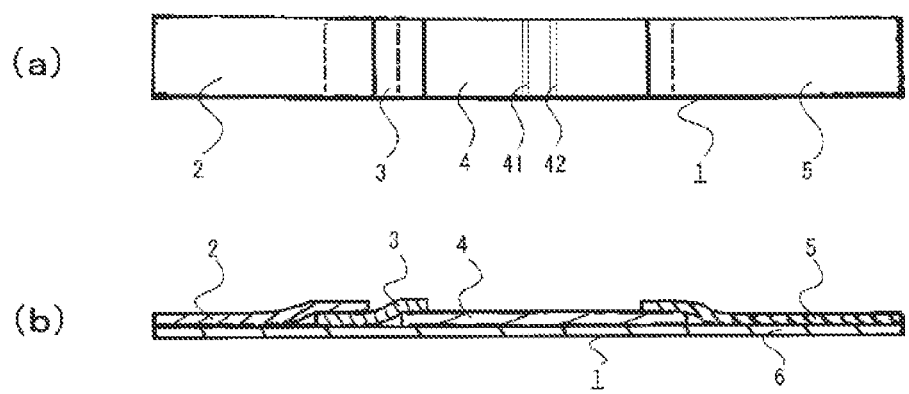

_US 10,466,234 B2_

METHOD OF PRODUCING LABELED ANTIBODY

CROSS-REFERENCE TO RELATED APPLICATIONS

This application is a continuation of PCT/JP2014/051990 filed on Jan. 29, 2014 which claims benefit of Japanese Patent Application No. 2013-19972 filed on Feb. 4, 2013, the subject matters of which are incorporated herein by reference in their entirety.

TECHNICAL FIELD

The present invention relates to a method of producing a labeled antibody.

BACKGROUND ART

Fine particles that are from several nanometers to about 1 micrometer in diameter have been recently applied in various fields and attracted attention. The above-described fine particles include, for example, porous silica particles and zeolite particles which are used for an adsorbent or a catalyst, carbon black, metal oxide particles and inorganic compound particles which are used for a pigment, metal nanoparticles which are used for a conductive material, and silica particles which are used for a reinforcing agent of resin, and thus, material and use of the fine particles are wide-ranging. Moreover, with regard to semiconductor nanoparticles, silica nanoparticles containing a fluorochrome, and so forth, an application as new labeling particles is expected particularly in a field of biotechnology. In addition, silica nanoparticles containing a pigment with high concentration have a high molar extinction coefficient, and thus, an application thereof as further highly sensitive labeling particles is expected.

The above-described labeling particles can be used as a labeling reagent that can be used for detection, quantitative determination, dyeing or the like of a target molecule, by bonding a biomolecule (protein, nucleic acid or the like) having bonding capability with a specific target molecule on the surface of the particles.

SUMMARY OF INVENTION

The present invention is contemplated for providing a method of producing a labeled antibody having a structure in which an antibody bonds onto a surface of silica nanoparticles containing a functional molecule such as a fluorescent dye (hereinafter, referred to as functional molecule-containing silica nanoparticles), wherein the method is for producing the labeled antibody showing reduced nonspecific adsorption and enhanced capturing efficiency of a target antigen being a subject of detection (bonding efficiency with the target antigen) in immunoassay.

Moreover, the present invention is contemplated for providing a labeled antibody having a structure in which an antibody bonds onto functional molecule-containing silica nanoparticles, wherein the labeled antibody shows reduced nonspecific adsorption and enhanced capturing efficiency of a target antigen being a subject of detection in immunoassay.

The present inventors found that bonding capability of the labeled antibody produced by bonding the antibody onto the surface of the functional molecule-containing silica nanoparticles with the target antigen (capturing ability of the target antigen) significantly varies depending on a mode of bonding of the antibody onto the surface of the silica nanoparticles. Then, the present inventors found that, when the labeled antibody in the form of bonding a carboxyl group of the antibody with a thiol group on the surface of the silica nanoparticles through a linker molecule is used in the immunoassay, the nonspecific adsorption is significantly suppressed, and also the capturing ability of the target antigen is significantly improved. The present invention has been completed based on these findings.

The problems of the present invention have been solved by the following means.

<1> A method of producing a labeled antibody, including the steps of:

a) allowing silica nanoparticles containing a functional molecule and having a thiol group on a surface thereof, and a linker molecule containing a maleimido group and an amino group, to coexist in a solvent to form a thioether bond between the thiol group and the maleimido group, thereby obtaining functional molecule-containing silica nanoparticles on which the linker molecule is bonded; and b) allowing the functional molecule-containing silica nanoparticles on which the linker molecule is bonded, carbodiimide and an antibody to coexist in an aqueous solvent to form an amide bond between the amino group of the linker molecule and a carboxyl group of the antibody.

<2> The method according to the item <1>, wherein the antibody is selected from the group consisting of a fragment antibody, a single-stranded antibody and a diabody.

<3> The method according to the item <2>, wherein the fragment antibody is F(ab')$_2$ or Fab, and the single-stranded antibody is scFv, sc(FV)$_2$ or a polyamino acid containing a heavy chain variable region and a light chain variable region.

<4> The method according to the item <2> or <3>, wherein the antibody is the fragment antibody.

<5> The method according to any one of the items <1> to <4>, wherein the solvent used in the step a) is an aprotic solvent.

<6> The method according to the item <5>, wherein the aprotic solvent is selected from the group consisting of dimethylsulfoxide, sulfolane, pyridine, N-methylpyrrolidone, N-cyclohexylpyrrolidone, N,N-dimethylformamide and N,N-dimethylacetamide.

<7> The production method according to any one of the items <1> to <6>, wherein the linker molecule has a structure in which the maleimido group and the amino group are linked through a divalent aliphatic group or arylene group, or a combination thereof.

<8> The method according to any one of the items <1> to <7>, wherein a mean particle diameter of the labeled antibody is from 20 to 500 nm.

<9> The method according to any one of the items <1> to <8>, wherein the functional molecule is selected from the group consisting of a fluorescent molecule, a light-absorbing molecule, a magnetic molecule, a radioactive molecule and a pH-sensitive molecule.

<10> The method according to any one of the items <1> to <9>, wherein density of the thiol group present on the surface of the silica nanoparticles containing the functional molecule and having the thiol group on the surface thereof is from 0.002 to 0.2 piece/nm$^2$ and a bonding amount of the antibody is controlled by the amount of the thiol group.

<11> A labeled antibody having functional molecule-containing silica nanoparticles as labeled particles and having an antibody bonding on the surface thereof through a linker, wherein the functional molecule-containing silica nanoparticles and the linker are linked via a thioether bond, and <12> The labeled antibody according to the item <11>, wherein the antibody is selected from the group consisting of a fragment antibody, a single-stranded antibody and a diabody.

<13> The labeled antibody according to the item <12>, wherein the fragment antibody is F(ab')$_2$ or Fab, and the single-stranded antibody is scFv, sc(FV)$_2$ or a polyamino acid containing a heavy chain variable region and a light chain variable region.

<14> The labeled antibody according to the item <12> or <13>, wherein the antibody is the fragment antibody.

<15> The labeled antibody according to any one of the items <11> to <14>, wherein the linker has a divalent aliphatic group or arylene group, or a combination thereof.

<16> The labeled antibody according to any one of the items <11> to <15>, wherein a mean particle diameter of the labeled antibody is from 20 to 500 nm.

<17> Colloid in which the labeled antibody according to any one of the items <11> to <16> is dispersed in a dispersion medium.

<18> The colloid according to the item <17>, wherein the dispersion medium is a buffer.

<19> Analytical reagent containing the labeled antibody according to any one of the items <11> to <16>.

According to the production method of the labeled antibody of the present invention (hereinafter, simply referred to as the production method of the present invention), the labeled antibody in which nonspecific adsorption is further suppressed and the capturing ability of the target antigen is further improved in the immunoassay can be obtained. Moreover, according to the production method of the present invention, the amount of the bonded antibody is controlled by the amount of the thiol group on the surface of the functional molecule-containing silica nanoparticles, and therefore the amount of the antibody bonded on the surface of the silica nanoparticles can be further accurately controlled.

The labeled antibody of the present invention shows further reduced nonspecific adsorption in the immunoassay. On the other hand, the capturing ability of the target antigen is further enhanced. Moreover, in the labeled antibody of the present invention, the antibody is further strongly and stably bonded onto the surface of the functional molecule-containing silica nanoparticles by covalent bonding through the linker molecule, and therefore the antibody is hard to detach from the functional molecule-containing silica nanoparticles.

Other and further features and advantages of the invention will appear more fully from the following description, appropriately referring to the accompanying drawing.

BRIEF DESCRIPTION OF DRAWINGS

FIG. 1 is a drawing schematically showing structure of a test strip used in Example. In FIG. 1, (a) shows a top view and (b) shows a longitudinal sectional view.

MODE FOR CARRYING OUT THE INVENTION

The present invention is described in detail below based on preferred embodiments thereof.

In a production method of the present invention, silica nanoparticles containing a functional molecule and having a thiol group on a surface thereof are used. The silica nanoparticles have performance as so-called labeling particles. In the production method of the present invention, a specific linker molecule is allowed to bind covalently to the above-described silica nanoparticles through the thiol group present on the surface of the silica nanoparticles, and further, the antibody is allowed to bind covalently to another site of the linker molecule through a carboxyl group of the antibody. Thus, the labeled antibody having the antibody in an amount according to an amount of the thiol group present on the surface of the above-described silica particles can be obtained. The thus obtained labeled antibody can be used as an analytical reagent such as a diagnostic reagent and an inspection reagent.

"Functional molecule" in the above-described functional molecule-containing silica nanoparticles is not particularly limited, but a labeled molecule that may be a detection indicator in an analytical reagent or the like is preferably adopted. Specific examples of the functional molecule include a fluorescent molecule, a light-absorbing molecule, a magnetic molecule, a radioactive molecule and a pH-sensitive molecule, and one kind or two or more kinds thereof can be used.

The functional molecule-containing silica nanoparticles can be prepared by obtaining a product (organoalkoxysilane to which the functional molecule is bonded) in which the functional molecule and a silane coupling agent are bonded by a covalent bond, an ionic bond or any other chemical bond, or physical adsorption and allowing hydrolysis and polycondensation of this product with one kind or two or more kinds of silane compounds (siloxane component), for example, in an aqueous ammonia-containing solvent to form a siloxane bond.

As the above-described aqueous ammonia-containing solvent, a solution prepared by, for example, adding aqueous ammonia having a concentration of about 28%, to be from 0.2 to 3 wt % in an ammonia concentration, to a mixed solution in which water/ethanol are adjusted to be 1/10 to 1/1 in a volume ratio can be used.

The above-described silane compound (siloxane component) is not particularly limited, and for example, in addition to a tetraalkoxysilane such as tetraethoxysilane (TEOS) and tetramethoxysilane, γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane and 3-[2-(2-aminoethylamino)ethylamino]propyltriethoxysilane can be used. Among those, TEOS can be preferably used.

In addition, when one having the thiol group, such as MPS, is used as the above-described silane compound, the thiol group is present on the surface of the obtained functional molecule-containing silica nanoparticles, and therefore operation of introducing the thiol group onto the surface of the functional molecule-containing silica nanoparticles as described later is not always required.

In the case of allowing covalent bonding of a functional molecule with the silane coupling agent, for example, a functional molecule having an active group such as an N-hydroxysuccinimide (NHS) ester group, a maleimido group, an isocyanate group, an isothiocyanate group, an aldehydo group, a p-nitrophenyl group, a diethoxymethyl group, an epoxy group and a cyano group, and a silane coupling agent having a functional group (for example, an amino group, a hydroxyl group or a thiol group) that can react with these active groups can be used.

In the functional molecule having the NHS ester group, specific preferred examples in the case where the functional molecule is a fluorescent molecule include NHS ester group-containing fluorescence dye compounds such as 5-(and -6)-carboxytetramethylrhodamine NHS ester (trade name, manufactured by emp Biotech GmbH), DY550-NHS ester represented by the following formula and DY630-NHS ester represented by the following formula (trade name for both, manufactured by Dyomics GmbH), but the present invention is not limited thereto.

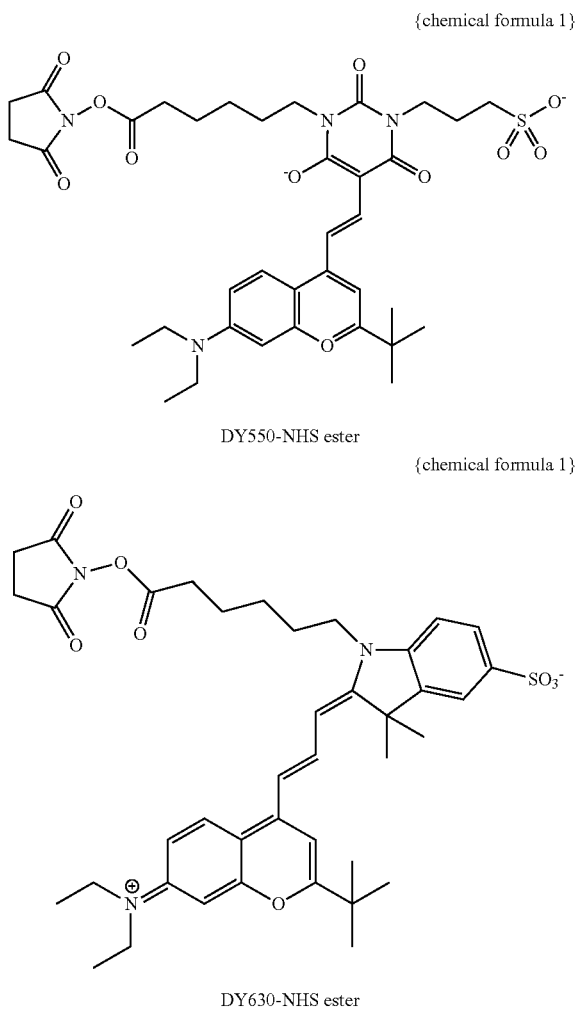

{chemical formula 1}

DY550-NHS ester

{chemical formula 1}

DY630-NHS ester

When the functional molecule has a succinimido group, the functional molecule can be bonded with a silane coupling agent having an amino group. Examples of the silane coupling agent having the amino group include γ-aminopropyltriethoxysilane (APS), 3-[2-(2-aminoethylamino)ethylamino]propyltriethoxysilane, 3-(2-aminoethylamino)propyldimethoxymethylsilane, 3-aminopropyltrimethoxysilane, and the like. Among them, APS can be preferably used.

A shape of the functional molecule-containing silica nanoparticles prepared as described above is spherical in which a ratio of a major axis to a minor axis is 2 or less. Moreover, a mean particle diameter is preferably 1 to 1,000 nm, and further preferably 20 to 500 nm.

The mean particle diameter can be determined, after occupied areas of composite particles are determined from projected areas of a total of 100 pieces of labeling particles randomly selected from images of Transmission Electron Microscope (TEM), Scanning Electron Microscope (SEM) or the like by means of an image processor, by calculating as a mean value (mean circle equivalent diameter) of a diameter of a circle equivalent to a value obtained by dividing the above total occupied areas by the number of pieces (100 pieces) of the selected composite particles.

Silica nanoparticles having an intended mean particle diameter can be obtained by ultrafiltration by using an ultrafiltration membrane such as YM-10 and YM-100 (trade names for both, manufactured by Millipore Corporation), or by recovering a supernatant or precipitates after performing centrifugal separation with suitable acceleration of gravity.

Subsequently, a method for introducing a thiol group onto the surface of the functional molecule-containing silica nanoparticles is explained.

Introduction of the thiol group onto the surface of the silica nanoparticles can be achieved by an ordinary method. For example, a method described in Journal of Colloid and Interface Science, 159, 150-157 (1993) or WO 2007/074722 A1 can be employed.

For example, the functional molecule-containing silica nanoparticles are dispersed into a mixed solvent of water and ethanol, and the silane coupling agent having the thiol group and aqueous ammonia are added thereto and the resultant mixture is stirred, thereby allowing introduction of the thiol group onto the surface of the functional molecule-containing silica nanoparticles.

The silane coupling agent having the thiol group preferably has structure in which the thiol group is bonded with a silicon atom through an alkylene group or an alkyleneoxy group. The number of carbon atoms in the alkylene group or the alkyleneoxy group is preferably from 2 to 10, further preferably 2 to 5, and still further preferably 2 to 4. As such a silane coupling agent, mercaptoalkyltrialkoxysilane is further preferred, and specific examples include 3-mercaptopropyltrimethoxysilane, 3-mercaptopropyltriethoxysilane, 3-mercaptopropylmethyldimethoxysilane and 11-mercaptoundecyltrimethoxysilane.

The above-described mixed solution of water and ethanol is preferably adjusted to be 1/10 to 1/1 in a volume ratio of water/ethanol. Moreover, a final concentration of the functional molecule-containing silica nanoparticles is preferably adjusted to from 0.1 to 2 wt %, and an amount of the silane coupling agent having the thiol group to be added thereto is preferably adjusted to from 0.2 to 20 mmol with respect to 1 g of the functional molecule-containing silica nanoparticles. Moreover, with regard to addition of aqueous ammonia, aqueous ammonia is preferably added to be from 0.2 to 3 wt % in an ammonia concentration by using, for example, an aqueous ammonia solution having a concentration of about 28%.

With regard to the method of introducing the above-described thiol group, the functional molecule-containing silica nanoparticles to be a core are prepared, and separated and washed, and then operation of introducing the thiol group thereonto is applied, and therefore time and expense are taken. Moreover, it is also difficult to introduce the thiol group thereonto in a desired amount and with high reproducibility. Ordinarily, in order to introduce the thiol group thereonto with high reproducibility, the silane compound having the thiol group is allowed to sufficiently react with the particles. However, this sufficient reaction causes excessive introduction amount of the thiol group introduced onto the surface of the functional molecule-containing silica nanoparticles, resulting in increasing hydrophobicity on the surface of the particles (more specifically, an absolute value of zeta potential is reduced) to easily cause aggregation among the particles.

Therefore, the functional molecule-containing silica nanoparticles having the thiol group are preferably prepared by employing a simpler method, and a method by which an amount of introducing the thiol group thereonto can be controlled freely and with high reproducibility.

Specific examples of such a preparation method include a method (continuous method) including the following steps.

(Continuous Method)

Mixing organoalkoxysilane to which a functional molecule is bonded, and tetraalkoxysilane in an aqueous ammonia-containing solvent to form core particles of silica containing the functional molecule in the solvent, thereby obtaining a dispersion of the core particles, and adding the silane coupling agent having the thiol group, and tetraalkoxysilane to the dispersion obtained in the above-described step to form a shell layer on the core particles of silica.

The amount of the thiol group to be introduced can be freely adjusted by adjusting an addition ratio of the above-described silane coupling agent having the thiol group to the above-described tetraalkoxysilane. As the tetraalkoxysilane, TEOS is preferred.

In the above-described continuous method, from preparation of the functional molecule-containing silica nanoparticles to introduction of the thiol group thereonto can be continuously performed, and therefore working time and also expense are significantly improved.

The absolute value of zeta ($\zeta$) potential in the functional molecule-containing silica nanoparticles into which the thiol group is introduced is preferably from 20 to 70 mV. With regard to the particles in which the absolute value of zeta potential is within the above-described range, aggregation is suppressed and dispersibility is further enhanced.

The zeta potential can be measured using Zetasizer Nano (trade name, manufactured by Malvern Instruments Ltd.), ELS-Z1 (trade name, manufactured by Otsuka Electronics Co., Ltd.) or NICOMP 380ZLS (trade name, manufactured by IBC Advanced Technologies, Inc.) or the like.

The amount of the thiol group present on the surface of the functional molecule-containing silica nanoparticles can be quantitatively determined, by a method described later, using a reagent color of which is developed by bonding to an SH group. The amount of the thiol group on the functional molecule-containing silica nanoparticles having the thiol group to be used in the present invention is preferably adjusted to from 0.002 to 0.2 piece/nm$^2$ in terms of density per unit surface area of the silica nanoparticles. When the density of the thiol group on the surface is smaller than 0.002 piece/nm$^2$, an amount of the biomolecule to be bonded through the linker molecule is small, and such a material is hard to function as the labeling reagent in several cases. Moreover, when the density of the thiol group is larger than 0.02 piece/nm$^2$, the hydrophobicity on the surface of the silica nanoparticles excessively increases to easily cause an increase in nonspecific adsorption due to hydrophobic interaction, and reduction of the dispersibility of the particles. The amount of the thiol group on the functional molecule-containing silica nanoparticles having the thiol group to be used in the present invention is preferably from 0.005 to 0.1 piece/nm$^2$, and further preferably from 0.01 to 0.05 piece/nm$^2$ in terms of the density per unit surface area of the silica nanoparticles.

(Quantitative Determination Method of Amount of Thiol Group on Surface of Silica Nanoparticles)

The amount of the thiol group on the surface of the silica nanoparticles can be quantitatively determined by using DNTB (5,5'-dithiobis(2-nitrobenzoic acid)) as a reagent. For example, as the quantitative determination method of the thiol group using DNTB, the determination can be made by applying the method described in Archives of Biochemistry and Biophysics, 82, 70 (1959). As one example of a specific method, 20 µL of solution of 10 mM DNTB dissolved in a phosphate buffer (pH 7.0), and 2.5 mL of silica nanoparticle colloid prepared in 200 mg/mL, are mixed, and after 1 hour, absorbance at 412 nm is measured, and then the thiol group can be quantitatively determined from a calibration curve prepared using γ-mercaptopropyltrimethoxysilane (MPS) as a reference material.

The linker molecule used in the present invention is not particularly limited, as long as the molecule contains a maleimido group and an amino group therein, and is preferably a molecule in which the maleimido group and the amino group are linked through a divalent aliphatic group or an arylene group, or a combination thereof. The number of carbon atoms in the above-described divalent aliphatic group is preferably an integer from 1 to 20, and further preferably an integer from 2 to 10. Moreover, as the above-described arylene group, phenylene is preferred.

The linker molecule preferably has the maleimido group and the amino group by one for each.

The molecular weight of the linker molecule used in the present invention is not particularly limited, but is preferably from 150 to 5,000.

Specific examples of the linker molecule having the maleimido group and the amino group within the molecule include N-(4-amino phenyl)maleimide, N-(2-aminoethyl)maleimide hydrochloride and N-acetylaminomaleimide, but the present invention is not limited thereto.

In the production method of the present invention, a thioether bond is first formed between the maleimido group of the above-described linker molecule, and the thiol group introduced onto the surface of the functional molecule-containing silica nanoparticles, thereby obtaining the functional molecule-containing silica nanoparticles on which the linker molecule is bonded.

A reaction of the maleimido group with the thiol group as described above can be performed in water or a buffer when the linker molecule to be used is salt such as hydrochloride. When the linker molecule to be used is not salt, the reaction is performed in an aprotic solvent. If a protic solution is used, the maleimido group reacts with a solvent molecule, resulting in reducing reactivity with the thiol group in several cases, and therefore the reactivity is higher when the aprotic solvent is used. The above-described aprotic solvent is not limited, as long as the silica nanoparticles may be dispersed thereinto, and the solvent is preferably a polar solvent. Specific examples of the polar aprotic solvent include dimethyl sulfoxide, sulfolane, pyridine, N-methylpyrrolidone, N-cyclohexylpyrrolidone, N,N-dimethylformamide and N,N-dimethylacetamide. Above all, N,N-dimethylformamide is preferred.

Ordinarily, in a biochemical field, the reaction of the maleimido group with the thiol group is performed using an aqueous solvent unavoidably in many cases in order to prevent reduction of activity of the biomolecule such as the antibody. However, in the production method of the present invention, the maleimido group only needs to be reacted with the thiol group of the functional molecule-containing silica nanoparticles, and needs no reaction with the biomolecule, and therefore the reaction of the maleimido group with the thiol group can be significantly efficiently performed in the aprotic solvent.

In the above-described reaction, a concentration of the functional molecule-containing silica nanoparticles having the thiol group in the solvent is preferably adjusted to be from 0.05 to 2% by mass, and from 0.1 to 5 mg of linker molecule is preferably allowed to react with 1 mg of the functional molecule-containing silica nanoparticles having the thiol group. The reaction temperature is preferably from 0 to 60° C., more preferably from 0 to 40'C. The reaction time is preferably 5 minutes or more, more preferably from 5 to 120 minutes.

When the antibody is bonded, via the linker, with the functional molecule-containing silica nanoparticles on which the linker molecule is bonded prepared as described above, the functional molecule-containing silica nanoparticles on which the antibody is bonded are prepared. Specifically, the above-described antibody and carbodiimide described later are allowed to coexist in the aqueous solvent to active-esterify the carboxyl group of the antibody and to form an amide bond between this active ester and the amino group of the linker molecule. This bonding reaction is also performed in the aqueous solvent. The active-esterification of the carboxyl group of the antibody by mixing the antibody with the carbodiimide may be performed before mixing of the antibody with the functional molecule-containing silica nanoparticles on which the linker molecule is bonded, or after the mixing thereof, or simultaneously with the mixing thereof.

More specifically, in the present invention, the phrase "the functional molecule-containing silica nanoparticles on which the linker molecule is bonded, the carbodiimide and the antibody are allowed to coexist in the aqueous solvent" is used in the meaning involving any of the following embodiments (a) to (d):

(a) an embodiment in which the functional molecule-containing silica nanoparticles on which the linker molecule is bonded, the carbodiimide and the antibody are simultaneously mixed in the aqueous solvent;

(b) an embodiment in which the antibody and the carbodiimide are allowed to previously coexist in the aqueous solvent, and then mixing the resultant mixture with the functional molecule-containing silica nanoparticles on which the linker molecule is bonded;

(c) an embodiment in which the functional molecule-containing silica nanoparticles on which the linker molecule is bonded and the antibody are allowed to previously coexist in the aqueous solvent, and then mixing the resultant mixture with the carbodiimide; and (d) an embodiment in which the functional molecule-containing silica nanoparticles on which the linker molecule is bonded, and the carbodiimide are allowed to previously coexist in the aqueous solvent, and then mixing the resultant mixture with the antibody.

The above-described antibody includes immunoglobulin (whole antibody), F(ab')$_2$ or Fab obtained by performing enzymolysis thereof, scFv or sc(Fv)$_2$ in which a heavy chain variable region (VH) and a light chain variable region (VL) are linked in tandem through the linker, a diabody formed of 2 units in which VH and VL are linked through the linker, artificially chemically synthesized polyamino acid containing VH and VL, recombinant protein or recombinant polyamino acid containing VH and VL produced by using Escherichia coli, yeast or the like as an expression system. More specifically, "antibody" in the present invention means a molecule or unit having VH and VL, and a structure thereof is not limited, as long as the antibody has VH and VL.

The above-described aqueous solvent is not particularly limited, and is preferably a buffer, and an ordinary aqueous buffer such as a phosphate buffer, a borate buffer and a carbonate buffer can be used.

The above-described carbodiimide is not particularly limited, and one ordinarily used for active-esterification of the carboxyl group can be employed. For example, 1-ethyl-3-(3-dimethylaminopropyl)carbodiimide or the like can be used. Moreover, N-hydroxysuccinimide, sulfo-N-hydroxysuccinimide or the like may be allowed to coexist with the carbodiimide, in doing so, a further stable active ester group may be derived from an active ester group induced by the carbodiimide.

In the amide bonding reaction of the antibody with the linker molecule bonded to the functional molecule-containing silica nanoparticles, the reaction is preferably performed by allowing from 10 to 500 µg of the antibody to coexist with 1 mg of the functional molecule-containing silica nanoparticles on which the linker molecule is bonded.

The reaction temperature is preferably from 0 to 60'C, more preferably from 10 to 40'C. The reaction time is preferably 5 minutes or more, more preferably from 5 to 600 minutes.

When the reaction is performed through the above-mentioned steps, the functional molecule-containing silica nanoparticles on which the antibody is bonded, namely, the labeled antibody, is obtained in the aqueous solvent.

In order to extinguish reactivity of the active ester remaining in the labeled antibody as obtained above, bovine serum albumin, casein or the like may be further added thereto and mixed.

In the labeled antibody as prepared by the production method of the present invention, the amount of the antibody bonded to the surface of the functional molecule-containing silica nanoparticles can be measured by an ordinary method. For example, the bonding amount can be quantitatively determined by UV method, Lowry method, or Bradford method.

The mean particle diameter of the labeled antibody prepared by the production method of the present invention is preferably from 1 to 1,000 nm, more preferably from 20 to 500 nm.

The mean particle diameter means an average value of equivalent circle diameter (average equivalent-circle diameter). The equivalent circle corresponds to the value obtained by measuring the occupied area of the particles using an image processing equipment based on the project area of the total 50 pieces of randomly-selected particles selected from an image obtained under transmission electron microscope (TEM) or scanning electron microscope (SEM) or the like, and dividing the total occupied area with the number of the selected particles (50 pieces).

The mean particle diameter does not reflect diameter of secondary particle formed by aggregation of primary particles.

In the labeled antibody prepared by the production method of the present invention, the variation coefficient, what is called CV value, of the particle diameter distribution is not particularly limited, and preferably 10% or less, and more preferably 8% or less.

In the labeled antibody as prepared by the production method of the present invention, the bonding amount of the antibody shows a positive correlation with the amount of the thiol group introduced onto the functional molecule-containing silica nanoparticles, and therefore the bonding amount of the antibody can be precisely controlled by controlling the introducing amount of the thiol group. For example, the amount of the thiol group on the surface of the particles is constant among the functional molecule-containing silica nanoparticles having the thiol group prepared under specific identical conditions, and therefore the functional molecule-containing silica nanoparticles having a predetermined amount of antibody can be consistently obtained. Thus, upon using the functional molecule-containing silica nanoparticles on which the antibody is bonded for an intended detection test or analytical test, a fluctuation of an obtained output value (for example, fluorescence intensity) can be significantly suppressed, and thus a test that is excellent in quantitative properties and reliability can be conducted. Moreover, when the amount of the thiol group on the surface of the functional molecule-containing silica nanoparticles is measured, the bonding amount of the antibody can be estimated. Accordingly, if a plurality of samples of functional molecule-containing silica nanoparticles each of which has different bonding amount of the thiol group are prepared, the functional molecule-containing silica nanoparticles on which an intended amount of the antibody is bonded can be prepared according to a purpose.

In the production method of the present invention, the antibody bonds to the functional molecule-containing silica nanoparticles through the carboxyl group of the antibody. More specifically, on the surface of the functional molecule-containing silica nanoparticles, the antibody bonded thereon via the amide bond between a carboxyl terminal (C-terminus) in an amino acid sequence of the antibody and the amino group of the linker molecule comes to exist in a large amount. As a result of this, a variable region of the antibody is easily aligned on a side opposite to the silica particles (outside the silica particles) or the like, and thus capturing ability of a target antigen is thought to be improved.

Improvement in the capturing ability of the target antigen becomes further significant when an antibody having lower molecular weight is used. For example, the ability is further significant when a fragment antibody such as a F(ab')$_2$ antibody and a Fab antibody, a single-stranded antibody such as scFv and sc(Fv)$_2$, and polyamino acid containing VH and VL are used as the antibody.

In the production method of the present invention, the functional molecule-containing silica nanoparticles having the thiol group on the surface thereof is used. By using the functional molecule-containing silica nanoparticles having the thiol group, the antibody and the functional molecule-containing silica nanoparticles can be easily and uniformly bonded. As a method for strongly and stably bonding the functional molecule-containing silica nanoparticles with the antibody through a linker molecule, for example, a method can also be considered in which an amino group is introduced onto the surface of the functional molecule-containing silica nanoparticles, in place of the thiol group, to allow covalent bonding between an active ester group of the linker molecule and the amino group, and further to allow covalent bonding between an maleimido group of the linker molecule and a thiol group of the antibody. However, practically, the functional molecule-containing silica nanoparticles, on the surface of which the amino group is introduced, significantly aggregate, and have poor usefulness. The reason may be that the silica nanoparticles having the amino group on the surface thereof has further increased hydrophobicity as compared to the silica nanoparticles having the thiol group on the surface thereof.

In the production method of the present invention, as the linker molecule, one having various carbon chain length or one including an aromatic ring can be selected. When a structure of the linker molecule is appropriately selected, targeted antigen capturing ability of the antibody bonded on the surface of the functional molecule-containing silica nanoparticles can be effectively educed.

The labeled antibody of the present invention is particles that may be obtained by the above-mentioned production method of the present invention. The labeled antibody of the present invention contains as labeling particles the functional molecule-containing silica nanoparticles, and has the antibody bonded onto the surface of the functional molecule-containing silica nanoparticles through the linker. The functional molecule-containing silica nanoparticles and the linker are linked via the thioether bond, and linked structure of the above-described antibody and the above-described linker is represented by *—C(=O)—NH—** (wherein, * represents a side of the antibody, and ** represents a side of the linker).

That is to say, the labeled antibody of the present invention has a structure in which the thiol group of the functional molecule-containing silica nanoparticles and the maleimido group of the linker molecule are bonded via the thioether bond, and a structure in which the amino group of the linker molecule and the carboxyl group of the antibody are bonded via the amide bond.

The functional molecule-containing silica nanoparticles having the thiol group, the linker molecule and the antibody are the same meaning as described in the above-mentioned production method of the present invention.

The labeled antibody of the present invention can be used as the labeling reagent and can be incorporated as the labeling reagent into various kinds of analytical reagents described later.

The labeled antibody of the present invention is excellent in the capturing ability of the target antigen. In addition, so-called nonspecific adsorption, which is not bonding due to an antigen-antibody reaction, is further suppressed. Analysis results obtained using the analytical reagent containing the labeled antibody of the present invention show high sensitivity and are excellent in reliability as shown in Examples described later.

The colloid according to the present invention is formed by dispersing the labeled antibody of the present invention into the dispersion medium.

The above-described dispersion medium is not particularly limited, and may be one that uniformly disperses the labeled antibody according to the present invention, but is preferably a hydrophilic solvent. Specific examples for the hydrophilic solvents include water, methanol, ethanol, a mixed solvent of water and methanol, a mixed solvent of water and ethanol, and a buffer solution such as PBS (phosphate buffered saline), a Tris buffer solution and an HEPES buffer solution.

Further, from a viewpoint of further preventing the nonspecific adsorption of the labeled antibody of the present invention, an arbitrary blocking agent such as polyethylene glycol (PEG) and bovine serum albumin (BSA) may be incorporated into the colloid according to the present invention. Moreover, a preservative such as sodium azide may be incorporated thereinto.

In the colloid according to the present invention, the labeled antibody according to the present invention stably exist, and the colloid can be stored for a long period of time with maintaining the antibody's capturing ability of the target antigen.

The colloid of the present invention may be used as a labeling reagent solution. Further, the colloid can be used for the preparation of labeled reagent contained in the analytical reagent.

The analytical reagent of the present invention contains the labeled antibody of the present invention. The analytical reagent of the present invention is used as a detection reagent for detecting a target antigen that may be recognized by the antibody, a quantitative determination reagent for quantitatively determining the target antigen, a separation reagent for separating the target antigen, a collection reagent for isolating and collecting the target antigen, a labeling reagent for labeling the target antigen, or the like.

The above-described target antigen is not particularly limited, and specific examples include a molecule to be a subject of detection in ordinary analysis, inspection and diagnosis. One example includes a viral antigen, a food allergen, various kinds of markers in a blood test, a toxin, a cell membrane protein, a cell membrane sugar chain and immunoglobulin.

Preferable examples of the analytical reagents according to the present invention include, for example, an immunochromatography device having a test strip in which the labeled antibody of the present invention are retained to a conjugate pad.

EXAMPLES

[Reference Example 1] Preparation of Functional Molecule-Containing Silica Nanoparticles Having Thiol Group-1

(Preparation of Functional Molecule-Containing Silica Nanoparticles)

Silica nanoparticles containing Carboxy Rhodamine-6G being a fluorescent molecule as a functional molecule were prepared.

In 10 mL dimethyl formamide (DMF), 31 mg of 5-(and -6)-carboxy rhodamine 6G-succinimidyl ester (trade name, manufactured by EMP Biotech GmbH) was dissolved. Then, 12 µL of APS (manufactured by Shin-Etsu Silicone Co., Ltd.) was added thereto and the reaction was carried out for 1 hour at room temperature (23° C.), to thereby obtain 5-(and -6)-carboxy rhodamine 6G-APS composite (5 mM).

600 µL of the obtained solution of 5-(and -6)-carboxy rhodamine 6G-APS composite mixed with 140 mL of ethanol, 6.5 mL of TEOS (manufactured by Shin-Etsu Silicone Co., Ltd.), 20 mL of distilled water, and 15 mL of 28 mass % aqueous ammonia, and the reaction was progressed at room temperature for 24 hours.

The reaction solution was centrifuged at a gravitational acceleration of 18.000×g for 30 minutes, and the supernatant was removed. To the precipitated functional molecule-containing silica nanoparticles, 4 mL of distilled water was added, dispersed the particles, and the dispersion was centrifuged again at a gravitational acceleration of 18,000×g for 30 minutes. Further, the washing operation was repeated twice additionally for removal of the unreacted TEOS, ammonia and others contained in the dispersion of silica nanoparticles containing the fluorescent molecule, and thus obtained 1.65 g of silica nanoparticles containing the fluorescent molecule having the mean particle diameter of 271 nm. Yield ratio ca. 94%.

(Introduction of Thiol Group)

Then, 1 g of particles obtained as described above was dispersed into 150 mL of mixed solution of water/ethanol=1/4. There, 1.5 mL of MPS (manufactured by Wako Pure Chemical Industries, Ltd.) was added. Subsequently, 20 mL of 28% aqueous ammonia was added thereto, and the resultant mixture was mixed at room temperature for 4 hours.

The reaction solution was centrifuged at a gravitational acceleration of 18,000×g for 30 minutes, and the supernatant was removed. To silica nanoparticles precipitated, 10 mL of distilled water was added to disperse the particles, and the resultant mixture was again centrifuged at a gravitational acceleration of 18,000×g for 30 minutes. The present washing operation was further repeated twice to remove unreacted MPS, ammonia and so forth that were contained in a dispersion liquid of fluorescent molecule-containing silica nanoparticles having a thiol group, and thus fluorescent molecule-containing silica nanoparticles on which the thiol group is introduced (hereinafter, referred to as thiol group-introduced fluorescent silica nanoparticles A) were obtained.

(Quantitative Analysis of Thiol Group)

Then, 500 mg of the above-described thiol group-introduced fluorescent silica nanoparticles A was used to conduct a quantitative analysis of the thiol group by DNTB. As a result, density of the thiol group on a surface of the thiol group-introduced fluorescent silica nanoparticles A was 0.046 piece/nm$^2$.

[Reference Example 2] Preparation of Functional Molecule-Containing Silica Nanoparticles Having Thiol Group-2

Aqueous ammonia of 14 mass % was diluted by 5 times with ethanol, and thus 175 mL of aqueous ammonia-containing solvent was prepared. To the aqueous ammonia-containing solvent, 1.5 mL (6.75 mmol) of TEOS (manufactured by Shin-Etsu Silicone Co., Ltd.) and 1.5 mL of 5-(and 6-)Carboxy Rhodamine-6G-APS composite (5 mM) prepared in Reference Example 1 were added, and the resultant mixture was stirred at 40° C. for 30 minutes, to thereby obtain a solution in which core particles containing fluorescent molecules was formed (hereinafter, occasionally referred to as core fluorescent particle-containing solution).

To the above-described core fluorescent particle-containing solution, 1.5 mL (6.75 mmol) of TEOS (manufactured by Shin-Etsu Silicone Co., Ltd.), and 550 µL (5.5 µmol) of 5-(and 6-)Carboxy Rhodamine-6G-APS dissolved into dimethylformamide (DMF, manufactured by Wako Pure Chemical Industries, Ltd.) to be a concentration of 10 mM were further added. The resultant mixture was stirred at 40° C. for 30 minutes to form a shell layer on the core fluorescent particles, to thereby obtain a solution containing fluorescent molecule-containing silica nanoparticles (hereinafter. occasionally referred to as first fluorescent silica nanoparticles).

To the above-described first fluorescent silica nanoparticles-containing solution, 500 µL (2.26 mmol) of TEOS, and 265 µL (2.65 µmol) of 5-(and 6-)Carboxy Rhodamine-6G-APS dissolved into DMF to be a concentration of 10 mM were further added. The resultant mixture was stirred at 40° C. for 30 minutes to further form a shell layer on first fluorescent silica nanoparticles, to thereby obtain a solution containing particles (hereinafter. occasionally referred to as second fluorescent silica nanoparticles).

In order to introduce a mercaptopropyl group onto a surface of second fluorescent silica nanoparticles, 1 mL of mixed solution of MPS (manufactured by Wako Pure Chemical Industries, Ltd.) and TEOS (MPS/TEOS mixed solution) as prepared at the mixing ratio of conditions 1 in Table 1 was further added to the above-described second fluorescent silica nanoparticles-containing solution. The resultant mixture was stirred at room temperature for 30 minutes, to thereby obtain a solution containing fluorescent molecule-containing silica nanoparticles having a hydroxyl group and a mercaptopropyl group on the surface layer thereof (hereinafter, referred to as thiol group-introduced fluorescent silica nanoparticles B). In the same manner, solutions containing fluorescent molecule-containing silica nanoparticles prepared by adding MPS/TEOS mixed solutions prepared at the mixing ratios of conditions 2 and 3 in Table 1 (hereinafter referred to as thiol group-introduced fluorescent silica nanoparticles C and thiol group-introduced fluorescent silica nanoparticles D, respectively) were also prepared.

The MPS/TEOS mixed solution was prepared just before addition.

TABLE 1

|  | MPS concentration in mixture of MPS and TEOS(1 mL) | TEOS concentration in mixture of MPS and TEOS(1 mL) |
| --- | --- | --- |
| Condition 1 | 25 volume % (1.3 mmol) | 75 volume % (3.4 mmol) |
| Condition 2 | 50 volume % (2.7 mmol) | 50 volume % (2.3 mmol) |
| Condition 3 | 75 volume % (4.0 mmol) | 25 volume % (1.1 mmol) |

(Quantitative Analysis of Thiol Group)

Then, 500 mg of each thiol group-introduced fluorescent silica nanoparticles B to D prepared based on the conditions 1 to 3, respectively, was subjected to a quantitative analysis of the thiol group using DNTB. As a result, density of the thiol group on a surface was 0.012 piece/nm$^2$ in the case of the thiol group-introduced fluorescent silica nanoparticles B, 0.056 piece/nm$^2$ in the case of the thiol group-introduced fluorescent silica nanoparticles C, and 0.072 piece/nm$^2$ in the case of the thiol group-introduced fluorescent silica nanoparticles D.

[Comparative Example 1] Preparation of Labeled Antibody (Bonding Via Amino Group of Antibody-1)

To 40 μL of dispersion liquid (concentration 25 mg/mL, a dispersion medium: distilled water) of thiol group-introduced fluorescent silica nanoparticles A (mean particle diameter 260 nm) prepared in Reference Example 1, 460 μL of DMF was added, and the resultant mixture was centrifuged at a gravitational acceleration of 15,000×g for 10 minutes. A supernatant was removed, 500 μL of DMF was added thereto, the resultant mixture was centrifuged and a supernatant was removed. Then, 500 μL of DMF was again added to disperse thiol group-introduced fluorescent silica nanoparticles A. In there, 1 mg of 3-maleimidobenzoic acid as a linker molecule was added, the resultant mixture was mixed for 30 minutes, and thus a thioether bond was formed between the maleimido group of the above-described linker molecule and the thiol group of the thiol group-introduced fluorescent silica nanoparticles A.

This reaction mixture was centrifuged at gravitational acceleration of 15,000×g for 10 minutes, a supernatant was removed, and then 90.6 μL of distilled water was added to disperse particles. Subsequently, 100 μL of 0.5 M MES (2-morpholinoethane sulfonic acid) (pH 6.0), 230.4 μL of 50 mg/mL NHS (N-hydroxysuccinimide), 75 μL of 19.2 mg/mL EDC (1-ethyl-3-(3-dimethylaminopropyl)carbodiimide) were added thereto, and the resultant mixture was mixed. There, 4.0 μL of anti-influenza A nucleoprotein antibody (6.2 mg/mL, manufactured by HyTest, Ltd.) was added, and the resultant mixture was mixed for 10 minutes.

The resultant dispersion was centrifuged at a gravitational acceleration of 15,000×g for 10 minutes, and the supernatant was removed. There, 400 μL of 10 mM KH$_2$PO$_4$ (pH 7.5) was added to disperse particles. Subsequently, the resultant dispersion was centrifuged at a gravitational acceleration of 15,000×g for 10 minutes, and the supernatant was removed. Then, 400 μL of 10 mM KH$_2$PO$_4$ (pH 7.5) was again added to disperse particles, and thus colloid was obtained.

Protein quantitative determination was performed by using this colloid as a sample. For protein quantitative determination, Pierce BCA Protein Assay Kit (manufactured by Thermo Fisher Scientific K.K.) was used. As a result, the bonding amount of the antibody was 8.5 mg per 1 g of fluorescent molecule-containing silica nanoparticles on which the antibody was bonded.

Subsequently, 10 μL of 10% BSA was added to the above-described colloid, and the resultant mixture was mixed for 10 minutes. The resultant mixture was centrifuged at a gravitational acceleration of 15,000×g for 10 minutes, and the supernatant was removed. Then, 500 μL of 10 mM KH$_2$PO$_4$ (pH 7.5) was added to disperse particles, the resultant mixture was centrifuged at a gravitational acceleration of 15,000×g for 10 minutes, and a supernatant was removed. Then, 400 μL of 10 mM KH$_2$PO$_4$ (pH 7.5) was again added to disperse particles, to thereby obtain colloid in which functional molecule-containing silica nanoparticles bonded with the anti-influenza A nucleoprotein antibody (hereinafter, referred to as colloid A of the comparative example) were dispersed.

[Comparative Example 2] Preparation of Labeled Antibody (Bonding Via Amino Group of Antibody-2)

Bonding process of the antibody was performed by using thiol group-introduced fluorescent silica nanoparticles B to D prepared in Reference Example 2 in the same manner as the method in Comparative example 1, and thus each colloid in which particles were dispersed was obtained. As a result of protein quantitative determination, the bonding amount of the antibody per 1 g of fluorescent molecule-containing silica nanoparticles on which the antibody was bonded was 3.7 mg when the thiol group-introduced fluorescent silica nanoparticles B was used, 9.2 mg when the thiol group-introduced fluorescent silica nanoparticles C was used and 12.8 mg when the thiol group-introduced fluorescent silica nanoparticles D was used.

Subsequently, 10 μL of 10% BSA was added to the above-described each colloid, and each resultant mixture was mixed for 10 minutes. The resultant mixture was centrifuged at a gravitational acceleration of 15,000×g for 10 minutes, and the supernatant was removed. Then, 500 μL of 10 mM KH$_2$PO$_4$ (pH 7.5) was added to disperse particles, the resultant mixture was centrifuged at a gravitational acceleration of 15,000×g for 10 minutes, and a supernatant was removed. Then, 400 μL of 10 mM KH$_2$PO$_4$ (pH 7.5) was again added to disperse particles, to thereby obtain colloid in which functional molecule-containing silica nanoparticles bonded with the anti-influenza A nucleoprotein antibody (hereinafter, referred to as colloid B to D of the comparative examples, corresponding to the above-described thiol group-introduced fluorescent silica nanoparticles B to D, respectively) were dispersed.

[Example 1] Preparation of Labeled Antibody (Bonding Via Carboxyl Group of Antibody-1)

Bonding process of the antibody was performed by using thiol group-introduced fluorescent silica nanoparticles A prepared in the reference example 1, as follows.

To 40 µL of dispersion liquid (concentration 25 mg/mL, a dispersion medium: distilled water) of thiol group-introduced fluorescent silica nanoparticles A, 460 µL of DMF was added, and the resultant mixture was centrifuged at a gravitational acceleration of 15,000×g for 10 minutes. A supernatant was removed, 500 µL of DMF was added thereto, the resultant mixture was centrifuged and a supernatant was removed. Then, 500 µL of DMF was again added to disperse thiol group-introduced fluorescent silica nanoparticles A. In there, 1 mg of N-(4-amino phenyl)maleimide as a linker molecule was added, the resultant mixture was mixed for 30 minutes, and thus a thioether bond was formed between the maleimido group of the above-described linker molecule and the thiol group of thiol group-introduced fluorescent silica nanoparticles.

This reaction mixture was centrifuged at gravitational acceleration of 15,000×g for 10 minutes, a supernatant was removed, and then 90.6 µL of distilled water was added to disperse particles. Subsequently, 100 µL of 0.5 M MES (2-morpholinoethane sulfonic acid) (pH 6.0), 230.4 µL of 50 mg/mL NHS (N-hydroxysuccinimide) and 75 µL of 19.2 mg/mL EDC (1-ethyl-3-(3-dimethylaminopropyl)carbodiimide) were added thereto, and the resultant mixture was mixed. There, 4.0 µL of anti-influenza A nucleoprotein antibody (6.2 mg/ml, derived from mouse, manufactured by HyTest, Ltd.) was added, and the resultant mixture was mixed for 10 minutes.

The resultant mixture was centrifuged at gravitational acceleration of 15,000×g for 10 minutes, and a supernatant was removed. Then, 400 µL of 10 mM $KH_2PO_4$ (pH 7.5) was added thereto to disperse particles. Subsequently, the resultant dispersion was centrifuged at gravitational acceleration of 15,000×g for 10 minutes, and a supernatant was removed. Then, 400 µL of 10 mM $KH_2PO_4$ (pH 7.5) was again added thereto to disperse the particles, thereby obtaining colloid.

Protein quantitative determination was performed by using this colloid as a sample. For protein quantitative determination, Pierce BCA Protein Assay Kit (manufactured by Thermo Fisher Scientific K.K.) was used. As a result, the bonding amount of the antibody was 7.9 mg per 1 g of fluorescent molecule-containing silica nanoparticles on which the antibody was bonded.

Subsequently, 10 µL of 10% BSA was added to the above-described colloid, and the resultant mixture was mixed for 10 minutes. The resultant mixture was centrifuged at a gravitational acceleration of 15,000×g for 10 minutes, and the supernatant was removed. Then, 500 µL of 10 mM $KH_2PO_4$ (pH 7.5) was added to disperse particles, the resultant mixture was centrifuged at a gravitational acceleration of 15,000×g for 10 minutes, and a supernatant was removed. Then, 400 µL of 10 mM $KH_2PO_4$ (pH 7.5) was again added to disperse particles, to thereby obtain colloid in which functional molecule-containing silica nanoparticles on which the anti-influenza A nucleoprotein antibody was bonded (hereinafter, referred to as colloid A of the present invention) were dispersed.

[Example 2] Preparation of Labeled Antibody (Bonding Via Carboxyl Group of Antibody-2)

Bonding process of the antibody was performed by using thiol group-introduced fluorescent silica nanoparticles B to D prepared in Reference Example 2 in the same manner as the method in Example 1, and thus each colloid into which particles were dispersed was obtained. As a result of protein quantitative determination, the bonding amount of the antibody per 1 g of fluorescent molecule-containing silica nanoparticles on which the antibody was bonded was 4.2 mg when thiol group-introduced fluorescent silica nanoparticles B were used, 8.8 mg when thiol group-introduced fluorescent silica nanoparticles C were used, and 11.3 mg when thiol group-introduced fluorescent silica nanoparticles D were used.

Subsequently, 10 µL of 10% BSA was added to the above-described each colloid, and each resultant mixture was mixed for 10 minutes. The resultant mixture was centrifuged at a gravitational acceleration of 15,000×g for 10 minutes, and the supernatant was removed. Then, 500 µL of 10 mM $KH_2PO_4$ (pH 7.5) was added to disperse particles, the resultant mixture was centrifuged at a gravitational acceleration of 15,000×g for 10 minutes, and a supernatant was removed. Then, 400 µL of 10 mM $KH_2PO_4$ (pH 7.5) was again added to disperse particles, to thereby obtain colloid in which functional molecule-containing silica nanoparticles on which the anti-influenza A nucleoprotein antibody was bonded (hereinafter, referred to as colloid B to D of the present invention, corresponding to the above-described thiol group-introduced fluorescent silica nanoparticles B to D, respectively) were dispersed.

[Test Example 1] Immunochromatography Test (Preparation of Test Strip for Immunochromatography)

An antibody-immobilized membrane was prepared by the following method.

At a position of about 6 mm from an end of a membrane (length 25 mm, trade name: Hi-Flow Plus120 Membrane, manufactured by Millipore Corporation), as a test line having a width of about 1 mm for influenza A, a solution ((50 mM $KH_2PO_4$, pH 7.0)+5% sucrose) containing 1 mg/mL of rabbit-derived anti-influenza A nucleoprotein antibody (polyclonal antibody, manufactured by our Company) was applied in an application amount of 0.75 µL/cm.

Subsequently, as a control line having a width of about 1 mm, a solution ((50 mM $KH_2PO_4$, pH 7.0), sugar-free) containing 1 mg/mL of goat-derived anti-mouse IgG antibody (AKP Goat anti-mouse IgG Antibody, manufactured by BioLegend, Inc.) was applied in an application amount of 0.75 µL/cm to dry the resultant applied material at 50° C. for 30 minutes. In addition, an interval between the test line and the control line was adjusted to 3 mm.

The above-described antibody-immobilized membrane, a sample pad (Glass Fiber Conjugate Pad (GFCP), manufactured by Millipore Corporation), and an absorbent pad (Cellulose Fiber Sample Pad (CFSP), manufactured by Millipore Corporation) were assembled on a backing sheet (trade name AR9020, manufactured by Adhesives Research, Inc.). The membrane was provided such that the test line for influenza A was directed to a side of the sample pad and the control line was directed to a side of the absorbent pad.

(Detector)

A detector which had a detection unit composed of a light source, an optical filter and a photomultiplier tube (PMT) was prepared. The detection unit could linearly move at a constant speed by a motor. The detector was equipped with a recording mechanism of light-receiving intensity of PMT, and the recording was performed every 50 μseconds. The light source was a laser diode having a wavelength of 532 nm. A sample is irradiated with light from the laser diode and reflected light thorough an optical filter transmittable for only light having a wavelength of 550 nm or more was received in the photomultiplier tube (PMT).

(Rapid Judgment of Influenza Nucleoprotein)

A solution (50 mM $KH_2PO_4$, pH 7.0) of influenza A nucleoprotein having a concentration shown in Table 2 was prepared. Subsequently, a mixed liquid of 100 μL of this solution and 2 μL of colloid A (2.5 mg/mL) of the comparative example was added dropwise onto a sample pad portion of the test strip. A test was conducted on colloid B to D of the comparative examples and colloid A to D of the present invention in the same manner. After 15 minutes, measurement was carried out by the above-described detector and detected emission intensity of line was quantified. The results are shown in Table 2.

colloid as a sample, the bonding amount of antibody was 7.1 mg per 1 g of fluorescent molecule-containing silica nanoparticles to which the antibody was bonded.

Subsequently, 10 μL of 10% BSA was added to the above-described colloid, and the resultant mixture was mixed for 10 minutes. The resultant mixture was centrifuged at a gravitational acceleration of 15,000×g for 10 minutes, and the supernatant was removed. Then, 500 μL of 10 mM $KH_2PO_4$ (pH 7.5) was added to disperse particles, the resultant mixture was centrifuged at a gravitational acceleration of 15,000×g for 10 minutes, and a supernatant was removed. Then, 400 μL of 10 mM $KH_2PO_4$ (pH 7.5) was again added to disperse particles, to thereby obtain colloid in which functional molecule-containing silica nanoparticles on which the Fab of the anti-influenza A nucleoprotein antibody was bonded (hereinafter, referred to as colloid A' of the comparative example) were dispersed.

TABLE 2

| Influenza A nucleoprotein (ng/ml) | Colloid A | | | Colloid B | | |
|---|---|---|---|---|---|---|
| | Test-line intensity (a.u.) | | 100 × [(present invention) − (Comparative example)]/ (Comparative example) (%) | Test-line intensity (a.u.) | | 100 × [(present invention) − (Comparative example)]/ (Comparative example) (%) |
| | Comparative example | Present invention | | Comparative example | Present invention | |
| 0 | 26 | 15 | −42% | 25 | 17 | −32% |
| 20 | 131 | 181 | 38% | 66 | 91 | 38% |
| 50 | 344 | 451 | 31% | 178 | 241 | 35% |

| Influenza A nucleoprotein (ng/ml) | Colloid C | | | Colloid D | | |
|---|---|---|---|---|---|---|
| | Test-line intensity (a.u.) | | 100 × [(present invention) − (Comparative example)]/ (Comparative example) (%) | Test-line intensity (a.u.) | | 100 × [(present invention) − (Comparative example)]/ (Comparative example) (%) |
| | Comparative example | Present invention | | Comparative example | Present invention | |
| 0 | 35 | 22 | −37% | 40 | 26 | −35% |
| 20 | 146 | 198 | 36% | 187 | 244 | 30% |
| 50 | 387 | 491 | 27% | 508 | 632 | 24% |

As shown in Table 2, when comparison is made on the colloid in which the identical thiol group-introduced fluorescent silica nanoparticles were used, in samples in which no influenza A nucleoprotein was contained (0 ng/mL), the test-line intensity was further suppressed and nonspecific adsorption was smaller in the case of using the colloid of the present invention in comparison with the case of using the colloid of the comparative example. On the other hand, in samples in which the influenza A nucleoprotein was contained (20 ng/mL and 50 ng/mL), the test-line intensity was significantly increased in the case of using colloid of the present invention in comparison with the case of using the colloid of comparative example.

[Comparative Example 3] Preparation of Labeled Antibody (Bonding Via Amino Group of Antibody-3)

As functional molecule-containing silica nanoparticles, the thiol group-introduced fluorescent silica nanoparticles A prepared in Reference Example 1 were used, and as an antibody, Fab of an anti-influenza A nucleoprotein antibody was used to bond the antibody to the silica particles in the same manner as Comparative example 1. As a result of quantitative determination of protein using the resultant

[Example 3] Preparation of Labeled Antibody (Bonding Via Carboxyl Group of Antibody-3)

As functional molecule-containing silica nanoparticles, the thiol group-introduced fluorescent silica nanoparticles A prepared in Reference Example 1 were used, and as an antibody, Fab of an anti-influenza A nucleoprotein antibody, which was identical with one used in Comparative example 3, was used to bond the antibody to the silica particles in the same manner as Example 1. As a result of quantitative determination of protein using the resultant colloid as a sample, the bonding amount of antibody was 8.5 mg per 1 g of fluorescent molecule-containing silica nanoparticles to which the antibody was bonded.

Subsequently, 10 μL of 10% BSA was added to the above-described colloid, and the resultant mixture was mixed for 10 minutes. The reaction solution was centrifuged at a gravitational acceleration of 15,000×g for 10 minutes, and the supernatant was removed. Then, 500 μL of 10 mM $KH_2PO_4$ (pH 7.5) was added to disperse particles, the resultant mixture was centrifuged at a gravitational acceleration of 15,000×g for 10 minutes, and a supernatant was removed. Then, 400 μL of 10 mM $KH_2PO_4$ (pH 7.5) was again added to disperse particles, to thereby obtain colloid in which functional molecule-containing silica nanoparticles on which the Fab of the anti-influenza A nucleoprotein antibody was bonded (hereinafter, referred to as colloid A' of the present invention) were dispersed.

[Test Example 2] Immunochromatography Test

An immunochromatography test was conducted in the same as Test Example 1. The results are shown in Table 3.

TABLE 3

| Influenza A nucleoprotein (ng/ml) | Test-line intensity (a.u.) | | Test-line intensity ratio (%) 100 × [(present invention) − (Comparative example)]/ (Comparative example) (%) |
|---|---|---|---|
| | Colloid A' of Comparative example | Colloid A' of present invention | |
| 0 | 27 | 6 | −78% |
| 20 | 92 | 167 | 82% |
| 50 | 197 | 387 | 96% |

As shown in Table 3, in samples in which no influenza A nucleoprotein was contained (0 ng/mL), the test-line intensity was significantly suppressed in the case of using the colloid of Example 3 in comparison with the case of using the colloid of Comparative example 3. Furthermore, in samples in which the influenza A nucleoprotein was contained (20 ng/mL and 50 ng/mL), the test-line intensity was significantly increased in the case of using the colloid of Example 3 in comparison with the case of using the colloid of Comparative example 3. When comparison is made between the results shown in Table 2 and the results shown in Table 3, in comparison with the case where an ordinary antibody (whole antibody) was bonded (Table 2), in the case where a fragment antibody was used (Table 3), between one in which the antibody was bonded to the silica particles via the amino group of the antibody, and one in which the antibody was bonded to the silica particles via the carboxyl group of the antibody, a difference in the test-line intensity was found to be larger in the latter case (Table 3). In general, when a living specimen such as a blood sample was applied as the sample, it is known that the nonspecific adsorption is suppressed and detection sensitivity is improved in the case of using a fragment antibody in comparison with the case of using a whole antibody. Therefore, the labeled antibody of the present invention which has still further advantages in the case where the fragment antibody is used may be a further useful inspection tool on an actual inspection site.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Test strip
2 Sample pad
3 Conjugate pad
4 Antibody-immobilized membrane
41 Judgment region (Test line)
42 Control line
5 Absorbent pad
6 Backing sheet

The invention claimed is:

1. A method of producing a labeled antibody, comprising the steps of:
    a) allowing silica nanoparticles comprising a functional molecule and comprising a thiol group on a surface thereof, and a linker molecule comprising a maleimido group and an amino group, to coexist in a solvent to form a thioether bond between the thiol group and the maleimido group, thereby obtaining functional molecule-containing silica nanoparticles on which the linker molecule is bonded; and
    b) allowing the functional molecule-containing silica nanoparticles on which the linker molecule is bonded, carbodiimide and an antibody to coexist in an aqueous solvent to form an amide bond between the amino group of the linker molecule and a carboxyl group of the antibody,
    wherein the linker molecule is selected from the group consisting of N-(4-amino phenyl)maleimide, N-(2-aminoethyl)maleimide hydrochloride, and N-acetylaminomaleimide.

2. The method according to claim 1, wherein the antibody is selected from the group consisting of a fragment antibody, a single-stranded antibody and a diabody.

3. The method according to claim 2, wherein the fragment antibody is F(ab')$_2$ or Fab, and the single-stranded antibody is scFv, sc(FV)$_2$ or a polyamino acid comprising a heavy chain variable region and a light chain variable region.

4. The method according to claim 2, wherein the antibody is the fragment antibody.

5. The method according to claim 1, wherein the solvent used in the step a) is an aprotic solvent.

6. The method according to claim 5, wherein the aprotic solvent is selected from the group consisting of dimethylsulfoxide, sulfolane, pyridine, N-methylpyrrolidone, N-cyclohexylpyrrolidone, N,N-dimethylformamide and N,N-dimethylacetamide.

7. The method according to claim 1, wherein a mean particle diameter of the labeled antibody is from 20 to 500 nm.

8. The method according to claim 1, wherein the functional molecule is selected from the group consisting of a fluorescent molecule, a light-absorbing molecule, a magnetic molecule, a radioactive molecule and a pH-sensitive molecule.

9. The method according to claim 1, wherein density of the thiol group present on the surface of the silica nanoparticles comprising the functional molecule and comprising the thiol group on the surface thereof is from 0.002 to 0.2 piece/nm$^2$, and a bonding amount of the antibody is controlled by the amount of the thiol group.

10. The method according to claim 1, wherein the linker molecule is selected from the group consisting of N-(2-aminoethyl)maleimide hydrochloride, and N-acetylaminomaleimide.

* * * * *